United States Patent
Jinwal et al.

(10) Patent No.: US 10,765,755 B1
(45) Date of Patent: *Sep. 8, 2020

(54) PREPARATION AND CHARACTERIZATION OF METHYLENE BLUE NANOPARTICLES FOR ALZHEIMER'S DISEASE AND OTHER TAUOPATHIES

(71) Applicants: Umesh Kumar Jinwal, Tampa, FL (US); Vijaykumar Bhadabhai Sutariya, Tampa, FL (US)

(72) Inventors: Umesh Kumar Jinwal, Tampa, FL (US); Vijaykumar Bhadabhai Sutariya, Tampa, FL (US)

(73) Assignee: University of South Florida, Tampa, FL (US)

( * ) Notice: Subject to any disclaimer, the term of this patent is extended or adjusted under 35 U.S.C. 154(b) by 704 days.

This patent is subject to a terminal disclaimer.

(21) Appl. No.: 14/548,996

(22) Filed: Nov. 20, 2014

Related U.S. Application Data

(60) Provisional application No. 61/906,728, filed on Nov. 20, 2013.

(51) Int. Cl.
*A61K 31/5415* (2006.01)
*A61K 47/48* (2006.01)
*A61K 9/51* (2006.01)

(52) U.S. Cl.
CPC ...... *A61K 47/48915* (2013.01); *A61K 9/5123* (2013.01); *A61K 31/5415* (2013.01)

(58) Field of Classification Search
CPC ............ A61K 47/48915; A61K 9/5123; A61K 31/5415
USPC ........................................................ 424/490
See application file for complete search history.

(56) References Cited

U.S. PATENT DOCUMENTS

| | | |
|---|---|---|
| 6,953,794 B2 | 10/2005 | Wischik et al. |
| 7,335,652 B2 | 2/2008 | Wishchik et al. |
| 7,446,096 B2 * | 11/2008 | Wang .................... A61K 9/127 424/1.21 |
| 7,534,786 B2 | 5/2009 | Wishchik et al. |
| 7,723,515 B1 | 5/2010 | DiMauro |
| 7,893,054 B2 | 2/2011 | Wishchik et al. |
| 7,906,643 B2 | 3/2011 | DiMauro |
| 8,067,380 B2 | 11/2011 | Wang et al. |
| 8,278,298 B2 | 10/2012 | Wishchik et al. |
| 8,609,652 B2 | 12/2013 | DiMauro |
| 8,765,742 B2 | 7/2014 | Hilfiker et al. |
| 2011/0111002 A1 * | 5/2011 | Pop ........................ C12N 13/00 424/422 |
| 2014/0148446 A1 | 5/2014 | Simpkins et al. |

FOREIGN PATENT DOCUMENTS

WO    WO 2007001448    *    1/2007

OTHER PUBLICATIONS

Grover et al. (J. Biomol. Res. Ther. 2013: vol. 2, Issue 2, 1000e113 (p. 1-3). (Year: 2013).*
Geldenhuys et al. (Journal of Drug Targeting, 2011: 19(9), 837-845) . (Year: 2011).*
Gura. Hope in Alzheimer's Fight Emerges from Unexpected Places. Nature Medicine. 2008. vol. 14 (No. 9): 894.
Barten and Albright. Therapeutic Strategies for Alzheimer's Disease. Molecular Neurobiology. 2008. vol. 37: 171-186.
Friedhoff et al., Structure of Tau Protein and Assembly into Paired Helical Filaments, Biochimica et Biophysica Acta. 2000. vol. 1502: 122-132.
Chu. Alzheimer's Disease: Early Diagnosis and Treatment. Hong Kong medical journal. 2012. vol. 18 (No. 3): 228-237.
Ward et al., Tau Oligomers and Tau Toxicity in Neurodegenerative Disease. Biochemical Society Transactions. 2012. vol. 40 (No. 4): 667-671.
Taniguchi et al., Inhibition of Heparin-Induced Tau Filament Formation by Phenothiazines, Polyphenols, and Porphyrins. The Journal of Biological Chemistry. 2005. vol. 280 (No. 9): 7614-7623.
Congdon et al., Methylthioninium Chloride (Methylene Blue) Induces Autophagy and Attenuates Tauopathy in vitro and in vivo. Autophagy. 2012. vol. 8 (No. 4): 609-622.
Pritchard et al., The Toxicity of Tau in Alzheimer Disease: Turnover, Targets and Potential Therapeutics. Journal of Cellular and Molecular Medicine. 2011. vol. 15 (No. 8): 1621-1635.
Schirmer et al., "Lest We Forget You—Methylene Blue . . . ". Neurobiology of Aging. 2011. vol. 32: 2325.e7-2325e.16.
Duan et al., Methylene Blue Blocks Cgmp Production and Disrupts Directed Migration of Microglia to Nerve Lesions in the Leech Cns. Journal of Neurobiology. 2003. vol. 57: 183-192.
Riha et al., Memory Facilitation by Methylene Blue: Dose-Dependent Effect on Behavior and Brain Oxygen Consumption. European Journal of Pharmacology. 2005. vol. 511: 151-158.

(Continued)

*Primary Examiner* — Alton N Pryor
(74) *Attorney, Agent, or Firm* — Michele L. Lawson; Nilay J. Choksi; Smith & Hopen, P.A.

(57) ABSTRACT

A delivery system of coated and uncoated nanoparticles (NP) for delivery of methylene blue (MB). The delivery system was developed using PLGA-based polymer that was repeatedly shown to be biocompatible and biodegradable. The parameters of synthesized NPs were within the suitable range for BBB permeation—specifically, the NPs were monodispersed, with slight negative charge, and with the size within 100-150 nm range suitable for intravenous delivery and delivery to the brain. The coating on the nanoparticle did not have a significant impact on the nanoparticle size and zeta potential. Based on the immunoblotting experiments using AD cellular model, the GSH coated NPs were better in reducing tau levels compared to MB solution. In vitro BBB Transwell permeation study showed eight fold higher MB-NP permeation compared to the MB solution over 24 hours.

8 Claims, 7 Drawing Sheets

(56) References Cited

OTHER PUBLICATIONS

Atamna et al., Methylene Blue Delays Cellular Senescence and Enhances Key Mitochondrial Biochemical Pathways. Faseb Journal. 2008. vol. 22: 703-712.

Deiana et al., Methylthioninium Chloride Reverses Cognitive Deficits Induced by Scopolamine: Comparison with Rivastigmine. Psychopharmacology. 2009. vol. 202: 53-65.

Harvey et al., Role of Monoamine Oxidase, Nitric Oxide Synthase and Regional Brain Monoamines in the Antidepressant-Like Effects of Methylene Blue and Selected Structural Analogues. Biochemical Pharmacology. 2010. vol. 80: 1580-1591.

Oz et al., Methylene Blue and Alzheimer's Disease. Biochemical Pharmacology. 2009. vol. 78: 927-932.

Khakpay et al., Potentiation of the Glutamatergic Synaptic Input to Rat Locus Coeruleus Neurons by P2x7 Receptors. Purinergic signalling. 2010. vol. 6: 349-359.

Hosokawa et al., Methylene Blue Reduced Abnormal Tau Accumulation in P301I Tau Transgenic Mice. PLOS ONE. 2012. vol. 7 (No. 12): e52389.

O'Leary et al., Phenothiazine-Mediated Rescue of Cognition in Tau Transgenic Mice Requires Neuroprotection and Reduced Soluble Tau Burden. Molecular Neurodegeneration. 2010. vol. 5: 45.

Albanese et al., The Effect of Nanoparticle Size, Shape, and Surface Chemistry on Biological Systems. Annu Rev Biomed Eng. 2012. vol. 14: 1-16.

Chaisri et al., Preparation and Characterization of Cephalexin Loaded Plga Microspheres. Curr Drug Deliv. 2009. vol. 6: 69-75.

Yadav and Sawant. Formulation Optimization of Etoposide Loaded Plga Nanoparticles by Double Factorial Design and Their Evaluation. Curr Drug Deliv. 2010. vol. 7: 51-64.

Muthu and Singh. Poly (D, L-Lactide) Nanosuspensions of Risperidone for Parenteral Delivery: Formulation and in-Vitro Evaluation. Curr Drug Deliv. 2009. vol. 6: 62-68.

Kumar et al., Pegylated Dendritic Architecture for Development of a Prolonged Drug Delivery System for an Antitubercular Drug. Curr Drug Deliv. 2007. vol. 4: 11-19.

Lockman et al., Brain Uptake of Thiamine-Coated Nanoparticles. J Control Release. 2003. vol. 93: 271-282.

Geldenhuys et al., Brain-Targeted Delivery of Paclitaxel Using Glutathione-Coated Nanoparticles for Brain Cancers. J Drug Target. 2011. vol. 19 (No. 9): 837-845.

Kreuter. Nanoparticulate Systems for Brain Delivery of Drugs. Adv Drug Deliv Rev. 2001: vol. 47: 65-81.

Xie et al., Nanoparticulate Formulations for Paclitaxel Delivery across Mdck Cell Monolayer. The 13th Asia Pacific Confederation of Chemical Engineering Congress (APCChE). 2010: 1-2.

Olivier et al., Synthesis of Pegylated Immunonanoparticles. Pharmaceutical Research. 2002. vol. 19 (No. 8): 1137-1143.

Olivier et al., Indirect Evidence That Drug Brain Targeting Using Polysorbate 80-Coated Polybutylcyanoacrylate Nanoparticles Is Related to Toxicity. Pharmaceutical Research. 1999. vol. 16 (No. 12): 1836-1842.

Carroll et al., Brain-Targeted Delivery of Tempol-Loaded Nanoparticles for Neurological Disorders. J Drug Targeting. 2010. vol. 18 (No. 9): 665-674.

Gratton et al., The Effect of Particle Design on Cellular Internalization Pathways. Proc Natl Acad Sci U S A. 2008. vol. 105 (No. 33): 11613-11618.

Lynch et al., Protein-Nanoparticle Interactions: What Does the Cell See?. Nat Nanotechnol. 2009. vol. 4: 546-547.

Elsaesser and Howard. Toxicology of Nanoparticles. Adv Drug Deliv Rev. 2012. vol. 64: 129-137.

Liu. Down-Regulation of Gamma-Glutamylcysteine Synthetase Regulatory Subunit Gene Expression in Rat Brain Tissue During Aging. Journal of Neuroscience Research. 2002. vol. 68: 344-351.

Parihar et al., Age-Related Decreases in Nad(P)H and Glutathione Cause Redox Declines before Atp Loss During Glutamate Treatment of Hippocampal Neurons. Journal of Neuroscience Research. 2008. vol. 86: 2339-2352.

Rebrin et al., Effects of Age and Caloric Intake on Glutathione Redox State in Different Brain Regions of C57bl/6 and Dba/2 Mice. Brain Research. 2007. vol. 1127: 10-18.

Robillard et al., Glutathione Restores the Mechanism of Synaptic Plasticity in Aged Mice to That of the Adult. PloS One. 2011. vol. 6 (No. 5): e20676.

Sasaki et al., Age-Related Changes of Glutathione Content, Glucose Transport and Metabolism, and Mitochondrial Electron Transfer Function in Mouse Brain. Nuclear Medicine and Biology. 2001. vol. 28: 25-31.

Geldenhuys et al., Brain-Targeted Delivery of Paclitaxel Using Glutathione-Coated Nanoparticles for Brain Cancers. Journal of drug targeting. 2011. vol. 19 (No. 9): 837-845.

Jinwal et al., Imbalance of Hsp70 Family Variants Fosters Tau Accumulation. The FASEB Journal. Apr. 2013. vol. 27: 1450-1459.

Park et al., Pegylated Plga Nanoparticles for the Improved Delivery of Doxorubicin. Nanomedicine: Nanotechnology, Biology, and Medicine. 2009. vol. 5: 410-418.

Sobal et al., Radioiodinated Methylene Blue—a Promising Agent for Melanoma Scintigraphy: Labelling, Stability and in vitro Uptake by Melanoma Cells. Anticancer Res. 2008. vol. 28: 3691-3696.

Jinwal et al., Chemical Manipulation of Hsp70 Atpase Activity Regulates Tau Stability. The Journal of Neuroscience. 2009. vol. 29 (No. 39): 12079-12088.

Abisambra et al., Allosteric Heat Shock Protein 70 Inhibitors Rapidly Rescue Synaptic Plasticity Deficits by Reducing Aberrant Tau. Biological Psychiatry. Sep. 1, 2013. vol. 74: 367-374.

Etame et al., Design and Potential Application of PEGylated Gold Nanoparticles with Size-Dependent Permeation Through Brain Microvasculature. Nanomedicine: Nanotechnology, Biology, and Medicine. 2011. vol. 7: 992-1000.

Garberg et al., In vitro Models for the Blood-Brain Barrier. Toxicol in Vitro. 2005. vol. 19. 299-334.

Rempe et al., Transport of Poly(N-Butylcyano-Acrylate) Nanoparticles across the Blood-Brain Barrier in vitro and Their Influence on Barrier Integrity. Biochemical and Biophysical Research Communications. 2011. vol. 406: 64-69.

Pardridge. Blood-Brain Barrier Delivery. Drug discovery today. 2007: vol. 12 (No. 1-2): 54-61.

Pardridge. Blood-Brain Barrier Drug Targeting: The Future of Brain Drug Development. Molecular Interventions. 2003. vol. 3 (No. 2): 90-105, 151.

Saija et al., Changes in the Permeability of the Blood-Brain Barrier Following Sodium Dodecyl Sulphate Administration in the Rat. Experimental brain research. 1997. vol. 115: 546-551.

Koziara et al., In Situ Blood-Brain Barrier Transport of Nanoparticles. Pharmaceutical Research. 2003. vol. 20 (No. 11): 1772-1778.

Costantino et al., Is There a Clinical Future for Polymeric Nanoparticles as Brain-Targeting Drug Delivery Agents? Drug discovery today. 2012. vol. 17 (No. 7-8): 367-378.

Mu and Feng. A Novel Controlled Release Formulation for the Anticancer Drug Paclitaxel (Taxol): Plga Nanoparticles Containing Vitamin E Tpgs. J Control Release. 2003. vol. 86: 33-48.

Wischke and Schedndeman. Principles of Encapsulating Hydrophobic Drugs in Pla/Plga Microparticles. Int J Pharm. 2008. vol. 364: 298-327.

Jinwal et al., Methylene blue loaded nanoparticles for treatment of Alzheimer's disease and other tauopathies, Nanoflorida 2012, Sep. 29, 2012, USF, Tampa, FL.

Tang et al., Photodynamic Characterization and in Vitro Application of Methylene Blue Containing Nanoparticle Platforms. Photochemistry and Photobiology. 2005. vol. 81: 242-49.

Collins et al., Nanotechnology in Neurosurgery. Journal of Nanotechnology in Engineering and Medicine. 2010. vol. 1: 034001.

Danhier, F. et al., PLGA-based nanoparticles: An overview of biomedical applications, Journal of Controlled Release, Jul. 20, 2012, vol. 161, Issue 2, pp. 505-522.

Gaillard, P. J. et al., Enhanced brain delivery of liposomal methylprednisolone improved herapeutic efficacy in a model of neuroinflammation, Journal of Controlled Release, Dec. 28, 2012, vol. 164, Issue 3, pp. 364-369.

Rotman, M. et al., Enhanced glutathione PEGylated liposomal brain delivery of an anti-amyloid single domain antibody fragment in a

(56) References Cited

OTHER PUBLICATIONS mouse model for Alzheimer's disease, Journal of Controlled Release, Apr. 10, 2015, vol. 203, pp. 40-50.

Sercombe, L. et al., Advances and Challenges of Liposome Assisted Drug Delivery, Frontiers in Pharmacology, Dec. 1, 2015, vol. 6, Article 286, pp. 1-13.

\* cited by examiner

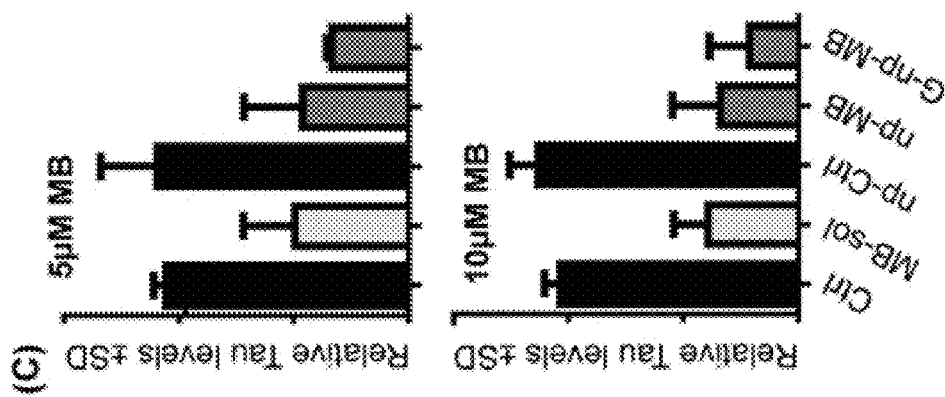
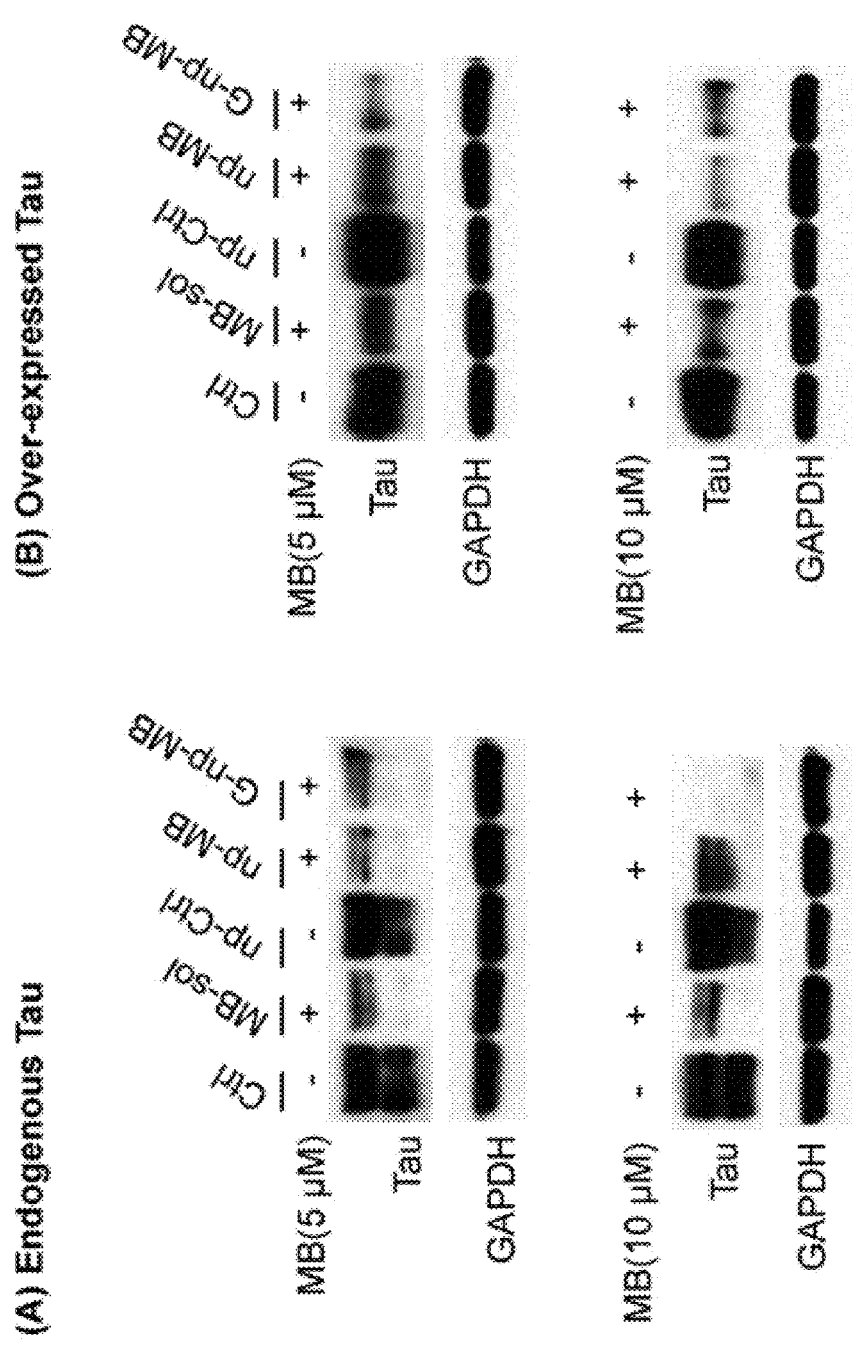
FIG. 4A
FIG. 4B
FIG. 4C

PREPARATION AND CHARACTERIZATION OF METHYLENE BLUE NANOPARTICLES FOR ALZHEIMER'S DISEASE AND OTHER TAUOPATHIES

BACKGROUND OF THE INVENTION

1. Field of the Invention

This invention relates, generally, to treatment and prevention of tauopathies. More specifically, it relates to nanoparticles with improved brain delivery for treatment of Alzheimer's disease and other related disorders.

2. Brief Description of the Prior Art

Alzheimer's disease (AD) is known as the most common form of dementia and with the increase in ageing population worldwide, the number of persons with dementia is also expected to increase. AD is associated with specific clinical and pathological features such as cognitive impairment and neurophsyciatric disturbances [1, 2]. Histological features of AD include extraneuronal β-amyloid plaques and intraneuronal neurofibrillary tangles [3, 4]. More specifically, neurofibrillary tangles consist of bundles of paired helical filaments comprising of abnormal aggregation of tau protein [3]. Tau is a neuronal microtubule-associated protein responsible for stabilization of axonal microtubules. Among other functions of tau protein are its role in signal transduction, plasma membrane and actin cytoskeleton interactions, neurite outgrowth, anchoring of enzymes, and regulation of vesicle transport [3]. However, at high concentration tau, oligomers exhibit toxicity and result in neurodegeneration [5].

Phenothiazines, such as methylene blue (MB), have been of interest due to its ability to inhibit tau filament formation and reduce the effects of oxidative stress; hence, MB is considered as a potential treatment for AD and other tauopathies [6-9]. MB is especially practical as possible therapeutic drug because of its well-characterized action of cGMP pathway inhibition and has been shown to improve oxygen consumption in the brain, repair mitochondrial function, and improve cellular metabolism [10-12]. Moreover, MB effects the three neurotransmitter systems important in AD, namely the following: cholinergic, resulting in improvement of memory [13]; serotonergic, resulting in antidepressant activity and increase of 5-hydroxyindole acetic acid (5-HIAA) [14]; and glutamatergic, resulting in enhanced memory retention and excitability [15, 16].

One of the challenges in targeting the brain in pharmaceutical therapy is the selectivity of the blood-brain barrier (BBB), which restricts most chemical agents from crossing into the brain tissue. MB is a highly hydrophilic molecule that limits its ability to cross the hydrophobic BBB, although limited and variable penetration has been demonstrated [17, 18]. Pharmacokinetic study on MB by Peter et al. suggests distribution of intravenously or orally-administered MB not only in the brain but also in various organs such as heart, lungs, liver, and kidneys, decreasing its bioavailability in the brain [19]. PLGA microspheres and nanoparticles (NP) have recently become of increased interest as efficient delivery vehicles for various drugs [20-22]. Further, successful outcomes have been reported in brain-targeted delivery using NPs with various coatings, such as TWEEN 80, thiamine, and conjugated with transferrin receptor specific antibody [24-30].

Targeting of the NPs to the brain by using reduced glutathione (GSH) coating is justified as the brain is particularly abundant in GSH transporters and GSH, an intracellular antioxidant that protects this organ from reactive oxygen species (ROS) generated by high oxygen consumption [23, 31-39]. Higher brain uptake of paclitaxel has been shown using the glutathione-coated nanoparticles in the mouse model [40]. Furthermore, localization of GSH in the brain has been demonstrated by numerous studies utilizing 99mTc meso-hexamethylpropyleneamineoxime (HMPAO) for labeling brain tissues. Thus, glutathione-coated particles as a drug delivery vehicle made of poly(lactic-co-glycolide) (PLGA)-b-PEG are postulated to be effective carrier for various drugs because of low toxicity, controlled drug release, and reduced uptake by reticulo-endothelial system (RES) in vivo as compared to unmodified PLGA [23][30].

However, distribution of methylene blue (MB) into the brain is still limited due to its high hydrophilicity. Accordingly, what is needed is a novel nanoparticle formulation of MB to improve its delivery to the brain, thus serving as an effective treatment option for Alzheimer's disease and other related disorders. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF DESCRIPTION OF THE DRAWINGS

For a fuller understanding of the invention, reference should be made to the following detailed description, taken in connection with the accompanying drawings, in which:

FIGS. 4A-4C depict nano-formulation of MB that reduce Tau. Cells were harvested and samples were analyzed for tau levels by immunoblotting. In FIG. 4A, endogenous Tau-expressing human neuroblastoma SHSY-5Y cells were treated with blank nanoparticles (np-Ctrl), MB-NPs (np-MB), GSM-coated NPs (G-np-MB), MB (in water, MB-sol), or vehicle (water, Ctrl) for 24 hours. In FIG. 4B, a similar experiment as in FIG. 4A was performed in HeLa cells stably transfected with human Tau (over-expressed tau). FIG. 4C is a quantitation plot of the immunoblots after GAPDH normalization. Statistical analyses across cell models demonstrated that MB in solution and MB associated with nano-particles each reduce tau levels slightly higher at 10 µM compared to 5 µM.

BRIEF SUMMARY OF THE INVENTION

Figure 1:
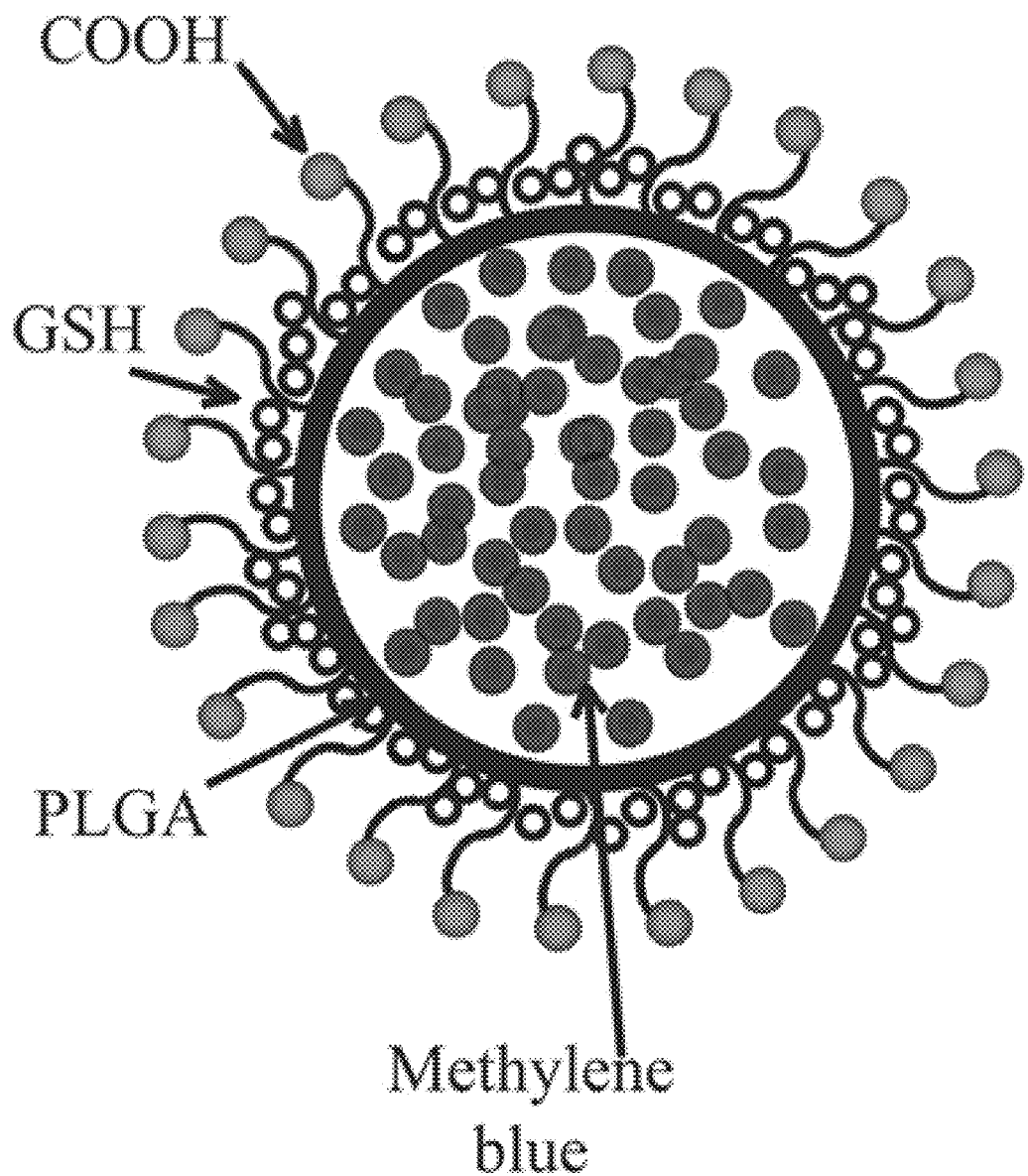
FIG. 1 depicts an exemplary structure of methylene blue loaded in a nanoparticle, according to an embodiment of the current invention. The nanoprecipitation method discussed herein allows for the polymer to form a spherical nanoparticle with methylene blue trapped inside. The PEG groups and carboxyl groups on the outside provide the specific properties. The GSH coating remains on the outside of the nanoparticle and allows for interactions with receptors. COOH refers to a carboxyl group; PEG refers to polyethylene glycol; and PLGA refers to poly(lactic-co-glycolic) acid.

The long-standing but heretofore unfulfilled need for a more effective delivery system of methylene blue is now met by a new, useful, and nonobvious invention.

In an embodiment, the current invention is a composition comprising methylene blue admixed with a polymeric-based layer of nanoparticles, wherein the layer of nanoparticles substantially encloses the methylene blue. The layer of nanoparticles includes an outer layer with an outer surface covalently modified by a spacer linked to a hydrophilic group, such that the spacer linked to the hydrophilic group extends outwardly from the outer surface of the outer layer of the layer of nanoparticles to facilitate penetration of the composition to a targeted region (e.g., brain) of a subject.

The layer of nanoparticles modified by the spacer linked to the hydrophilic group may be a PLGA-PEG-COOH structure.

The spacer may contain a hydrocarbon chain having a multiple bond, wherein the hydrocarbon chain contains an R group selected from the group consisting of a hydrogen, alkyl, alkenyl, alkynyl, alkoxy, hydroxylalkyl, hydroxyl, and haloalkyl.

The spacer may be selected from the group consisting of modified polyethylene glycols, propylene glycols, amino acids, peptides, chelators and polaxamers.

The hydrophilic group may be a carboxyl group.

The polymer-based layer of nanoparticles may include PLGA.

The outer surface of the layer of nanoparticles may be further modified by a hydrophobic, protective coating that facilitates distribution of the methylene blue in the targeted region of the subject.

The coating may be formed of glutathione, which permits controlled and sustained release of the methylene blue into the targeted region of the subject.

In a separate embodiment, the current invention is composition for effectively permeating or penetrating a blood-brain barrier of a subject. The composition comprises a pharmaceutical agent admixed with a polymeric-based layer of nanoparticles, wherein the layer of nanoparticles substantially encloses the pharmaceutical agent. The layer of nanoparticles includes an outer layer with an outer surface covalently modified by a spacer linked to a hydrophilic group, such that the spacer linked to the hydrophilic group extends outwardly from the outer surface of the outer layer of the layer of nanoparticles.

The outer surface of the layer of nanoparticles is further modified by a hydrophobic, protective glutathione coating that stabilizes the composition during permeation or penetration of the blood-brain barrier. The composition further has a (slight) negative charge.

The pharmaceutical agent may be methylene blue.

The layer of nanoparticles modified by the spacer linked to the hydrophilic group may be a PLGA-PEG-COOH structure.

The spacer may contain a hydrocarbon chain having a multiple bond, wherein the hydrocarbon chain contains an R group selected from the group consisting of a hydrogen, alkyl, alkenyl, alkynyl, alkoxy, hydroxylalkyl, hydroxyl, and haloalkyl.

The spacer may be selected from the group consisting of modified polyethylene glycols, propylene glycols, amino acids, peptides, chelators and polaxamers.

The hydrophilic group may be a carboxyl group.

The polymer-based layer of nanoparticles may include PLGA.

The composition may have a size or diameter of less than about 150 nm.

In a separate embodiment, the current invention is a composition for reduction of tau levels (e.g., treatment of Alzheimer's disease and related tauopathies) in a brain of a subject. The composition comprises methylene blue admixed with a polymeric-based layer of nanoparticles, wherein the layer of nanoparticles substantially encloses the methylene blue. The layer of nanoparticles includes an outer layer with an outer surface covalently modified by a spacer linked to a hydrophilic group, such that the spacer linked to the hydrophilic group extends outwardly from the outer surface of the outer layer of the layer of nanoparticles. The outer surface of the layer of nanoparticles is further modified by a hydrophobic, protective glutathione coating that stabilizes the composition during permeation or penetration of the blood-brain barrier. The glutathione coating also permits controlled or sustained release of the methylene blue in a brain of the subject.

The layer of nanoparticles modified by the spacer linked to the hydrophilic group may be a PLGA-PEG-COOH structure.

The spacer may contain a hydrocarbon chain having a multiple bond, wherein the hydrocarbon chain contains an R group selected from the group consisting of a hydrogen, alkyl, alkenyl, alkynyl, alkoxy, hydroxylalkyl, hydroxyl, and haloalkyl.

The spacer may be selected from the group consisting of modified polyethylene glycols, propylene glycols, amino acids, peptides, chelators and polaxamers.

The hydrophilic group may be a carboxyl group.

The polymer-based layer of nanoparticles may include PLGA.

The composition may have a size or diameter of less than about 150 nm.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Methylene blue (MB) has been shown to slow down the progression of the Alzheimer's disease (AD) and other tauopathies; however distribution of MB into the brain is limited due its high hydrophilicity. As a result of the challenges in MB delivery to the brain, an object of the current invention is to improve BBB penetration and MB cellular uptake in the brain and to decrease the systemic MB side effects. In an embodiment, a hydrophobic glutathione coated PLGA nanoparticles was developed to improve bioavailability of MB in the brain. Glutathione coated poly-(lactide-co-glycolide) (PLGA-b-PEG) nanoparticles (NPs) were prepared and tested in two different cell culture models of AD expressing microtubule associated protein tau (tau). The NPs showed a particle size averaging 136.5±4.4 nm, which is suitable for the blood brain barrier (BBB) permeation. The in vitro release profile of the NPs exhibited no initial burst release and showed sustained drug release for up to 144 hours.

In another embodiment, a delivery system for MB was developed for purpose of reducing tau levels in the human brain, in order to treat or prevent Alzheimer's disease and other tauopathies. Unexpectedly, treatment with newly formulated MB-NPs showed a potent reduction in both endogenous and overexpressed tau protein levels in human neuroblastoma SHSY-5Y cells expressing endogenous tau and transfected HeLa cells over-expressing tau protein, respectively. Furthermore, in vitro BBB Transwell study showed significantly higher permeation of MB-NP compared to the MB solution through the co-culture of rat brain endothelial 4 (RBE4) and C6 astrocytoma cells ($p<0.05$). The MB loaded nanoparticles could provide a more effective treatment option for AD and many other related disorders.

In an embodiment, a delivery system of coated and uncoated nanoparticles was developed using a PLGA-based polymer that was repeatedly shown to be biocompatible and biodegradable. The parameters of synthesized NPs were within the suitable range for BBB permeation; specifically, the NPs were monodispersed, with a slight negative charge, and with the size/diameter within 100-150 nm range suitable for intravenous delivery and delivery to the brain. The coating on the nanoparticle did not have a significant impact on the nanoparticle size and zeta potential. Based on the immunoblotting experiments using AD cellular model, the GSH-coated NPs were better in reducing tau levels compared to MB solution. In vitro BBB Transwell permeation study showed an eight-fold higher MB-NP permeation compared to the MB solution over 24 hours.

As used herein, the term "nanoparticle" refers to any polymeric micelle, lipid micelle, hybrid lipid-polymer micelle, liposome, niosomes, transferosome, liponanoparticle, lipid nanoparticles, nanostructured lipid nanocarriers (NLC), solid lipid nanoparticles (SLN), hybrid lipid-polymer nanoparticles, bicelle, polymerosomes, lamellar structures, and lipid vesicles, among other delivery systems that can be used suitably to deliver an active pharmaceutical agent, such as methylene blue.

Examples of polymers used to prepare nanoparticles include, but are not limited to, lipids or oils, gelatin, sodium alginate, gum arabic, starch, tragacanth, shellac, paraffin wax, poly (lactide-co-glycolide) (PLGA), polylactic acid (PLA), polycaprolactone (PCL), methyl cellulose, pectin, carrageenan, alginates, methyl cellulose, casein, bovine albumin serum, chitosan, hydroxypropyl cellulose, hydroxypropyl methyl cellulose, ethyl cellulose, cellulose acetate phthalate, carmellose, polyvinyl alcohol, polystyrene, polyurethane, polyvinylpyrrolidone, polymethacrylate, polyvinyl acetate, polyhydroxyethyl methacrylate, polyvinyl chloride, polyacrylate, polyacrylamide, polyethylene glycol, polyester, polyurea, and polyamide, among other suitable polymers that may be used to prepare the nanoparticles.

Examples of lipids that may be used include, but are not limited to, derivatives of glycerophospholipids, glycerolipids, sphingolipids, sterols, fatty acyl amides, prenols, ceramides, cholesterols, lecithin, glyceryl behenate (COMPRITOL), glyceryl palmitostearate (PRECIROL), glycerol monosterol (MONOSTEROL), glycerol disterate, sulfatides, phosphosphingolipids, phosphatidylcholines, phosphatidic acids, phosphatidylethanolamines, phosphatidylglycerols, phosphatidylserines, and phosphor lipids, among other suitable lipids that may be used to prepare nanoparticles.

Examples of oils that may be used include, but are not limited to, safflower oil, sesame oil, corn oil, castor oil, coconut oil, almond oil, cotton seed oil, soybean oil, olive oil, mineral oil, spearmint oil, clove oil, lemon oil, peppermint oil, triacetin, tributryin, ethyl butyrate, ethyl caprylateoleic acid, ethyl oleate, isopropyl myristate and ethyl caprylate, among other suitable oils that may be used to prepare nanoparticles.

The nanoparticles can be prepared using electrostatic interaction, self-assembly, ionotropic gelation, cross-linking, coacervation, homogenization-solvent evaporation, sonication, ultrasound, nanoprecipitation, spray drying, high pressure homogenization, layer by layer, freeze drying, hot-melt homogenization, film formation, co-solvent evaporation, high pressure instruments such as NANODEBEE, and coating or solvent emulsion methods, in combination or alone.

The surface of the nanoparticles can be modified with spacer linked to a hydrophilic group, enabling penetration of the BBB. Examples of spacers that can be used include, but are not limited to, hydrocarbon chains having one or more double bonds or triple bonds. More specifically, spacers may be modified or unmodified polyethylene glycols, propylene glycols, amino acids, peptides, chelators and polaxamers, among other known suitable spacers. Examples of chelators include, but are not limited to, saccharides, urea, DTPA, methyl cellulose, polyvinyl pyrrolidone, 1,2-Dioleoylsn-glycero-3-[(N-(5-amino-1-carboxypentyl) imidodiacetic acid) succinyl nickel salt] (DGS-NTA (Ni)) and EDTA, among other suitable chelators.

If a hydrocarbon chain is present, the hydrocarbon chain may be interrupted by —O—, —S—, —N(R)—, —N(R)—C(O)—O—, —O—C(O)—N(R)—, —O—C(O)—O—N(R)—, —N(R)—C(O)—N(R)—, —O—C(O)—O—, —P(R)—, —P(O)(R)—, and —C(O)—O(R)—. Each R, independently, may be aliphatic or aromatic. If aromatic, the compounds may include two (2) or more membered rings with or without heteroatoms. Examples of R can include, but would not be limited to, hydrogen, alkyl, alkenyl, alkynyl, alkoxy, hydroxylalkyl, hydroxyl, and haloalkyl. The interrupted hydrocarbon chain may be used for conjugation with each polymer or lipid.

As will become clearer as this specification continues, drug release from the nanoparticles can be immediate release or controlled release for the drug from the layer of nanoparticles. Particular polymers and/or lipids can be selected for immediate or controlled release of each drug from the layer of nanoparticles.

In the following non-limiting study, uncoated and glutathione-coated NPs containing MB were prepared and characterized for particle size, stability testing, in vitro drug release study, and their tau reducing function in cellular models of AD and other tauopathies. Although methylene blue is discussed herein as the pharmaceutical agent, any suitable pharmaceutical agent is contemplated by the current invention, whether used in tau level reduction or not.

Development of Coated and Uncoated MB-NPs, and Analysis Thereof

Figure 2:
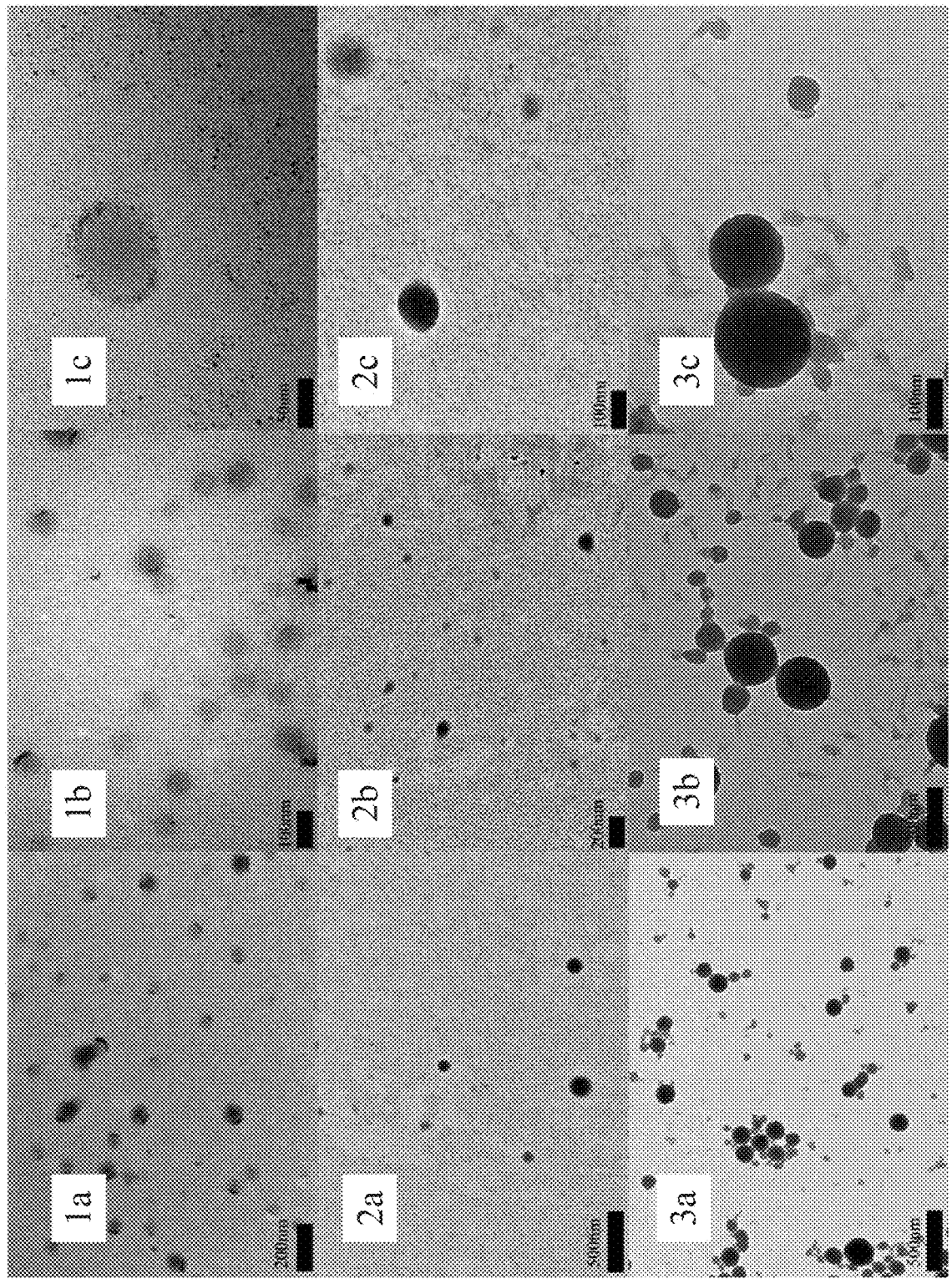
FIG. 2 depicts morphology of the nanoparticles by electron microscopy. In images 1a, 1b, and 1c, the NPs demonstrate consistent rounded morphology throughout the sample. The polymer and PEG groups are clearly visible in forming of the outer edge of the nanoparticle. In images 2a, 2b, and 2c, the MB-NPs also demonstrate consistent round shape and size. The loaded API is visible inside of the nanoparticle. In images 3a, 3b, and 3c, 2% GSH-coated MB-NPs retain the rounded appearance and remain consistent in the average size of the nanoparticle. GSH coating is obvious in forming the sharp edge outer edge of the nanoparticle with evidenced increase in the average nanoparticle size.

Blood-brain barrier (BBB) permeation is one of the key challenges in the field of pharmacy as most of large molecule pharmaceutics are incapable of crossing BBB [48-50]. Some of the drug delivery systems actually rely on the BBB disruption for permeation and delivery, especially in presence of solvents such as sodium dodecyl sulfate (SDS), ethanol, dimethylsulfoxide (DMSO), glycerol, and polysorbate-80 (TWEEN 80), which are often used in drug formulations [50-52]. However, disruption to the BBB may present toxicity as it may allow penetration of blood components, such as albumin, which are highly toxic, to the brain. In the current study, MB-NPs were developed to be used potentially for the treatment of Alzheimer's disease and other tauopathies. The glutathione-coated NPs were synthesized for the enhanced brain permeation due to abundance of GSH transporters present on the BBB [20-22, 31-34](FIGS. 1 and 2). The physical parameters of the NPs were studied in detail to ascertain suitability of the NPs properties for delivery across the BBB.

The average sizes/diameters of the NPs were within the 100-150 nm size range, which is appropriate for intravenous administration and blood brain barrier permeation [30, 53] (Table 1). The effect of the drug loading and the GSH coating on the average size of the nanoparticles was studied by light scattering, demonstrating decrease in size with MB-loading. The presence of GSH coating did not significantly alter the size of the NPs, which is important for tight control of the NPs characteristics to avoid potential unexpected adverse effects that may arise with variation of the NPs parameters, as the size of the nanoparticles can be an important factor in determining their uptake and toxicity, thus, narrow distribution of size may be desired [19, 31].

Further, the developed NPs had a slight negative charge as indicated by the negative zeta potential (Table 1). Presence of a slight negative charge allows the NPs to disperse in the solution and thus would remain in the blood stream for BBB permeation. The electrostatic repulsion prevents agglomeration that may potentially alter the interactions of NPs with their environment, which can, in turn, potentially induce toxicity [32].

The NPs demonstrated the ability to be stable in the PBS solution in the span of 5 days; the stability of the delivery system can be very important for successful targeting and crossing of the BBB (Table 2). No significant changes in the NPs sizes were detected. However, change in zeta potential was observed, perhaps due to the interactions of the nanoparticles with the salts of the PBS buffer. Unexpectedly, the GSH coating appears to have contributed to stability of the NPs, as the change of charge of the GSH-coated NPs was less drastic compared to the uncoated MB-NPs in the span of 5-day stability study (Table 2). GSH-coated nanoparticles demonstrated the least change of zeta potential—a finding consistent with the presence of GSH coating, which may limit the interaction of the NPs surface with its environment. The implications of maintenance of an intact GSH coat may be effective for targeted delivery and uptake of MB-NPs in the brain.

The NPs with entrapped drug are postulated to release the drug by diffusion, by surface erosion or bulk erosion of the polymer, and/or by swelling [54, 55]. There are three main stages of drug release: initial release phase, sustained release phase, and final polymer erosion accelerated phase. During the initial release phase, the drug on the surface of the NPs is released into the release medium. The sustained release phase follows due to diffusion of the drug out of the NPs, which is mainly influenced by the molecular weight of the drug and the porosity of the NPs wall. Finally, the accelerated phase occurs as the polymer erodes in connection with the glass transition temperature of the polymer and the interaction of the drug with the polymer. Therefore, the rate of release can be regulated by adjustment of the parameters relating to the properties of the NPs wall, such as polymer chain length, flexibility, mobility, swelling, and/or interactions between the active ingredient and the polymer.

Figure 3:
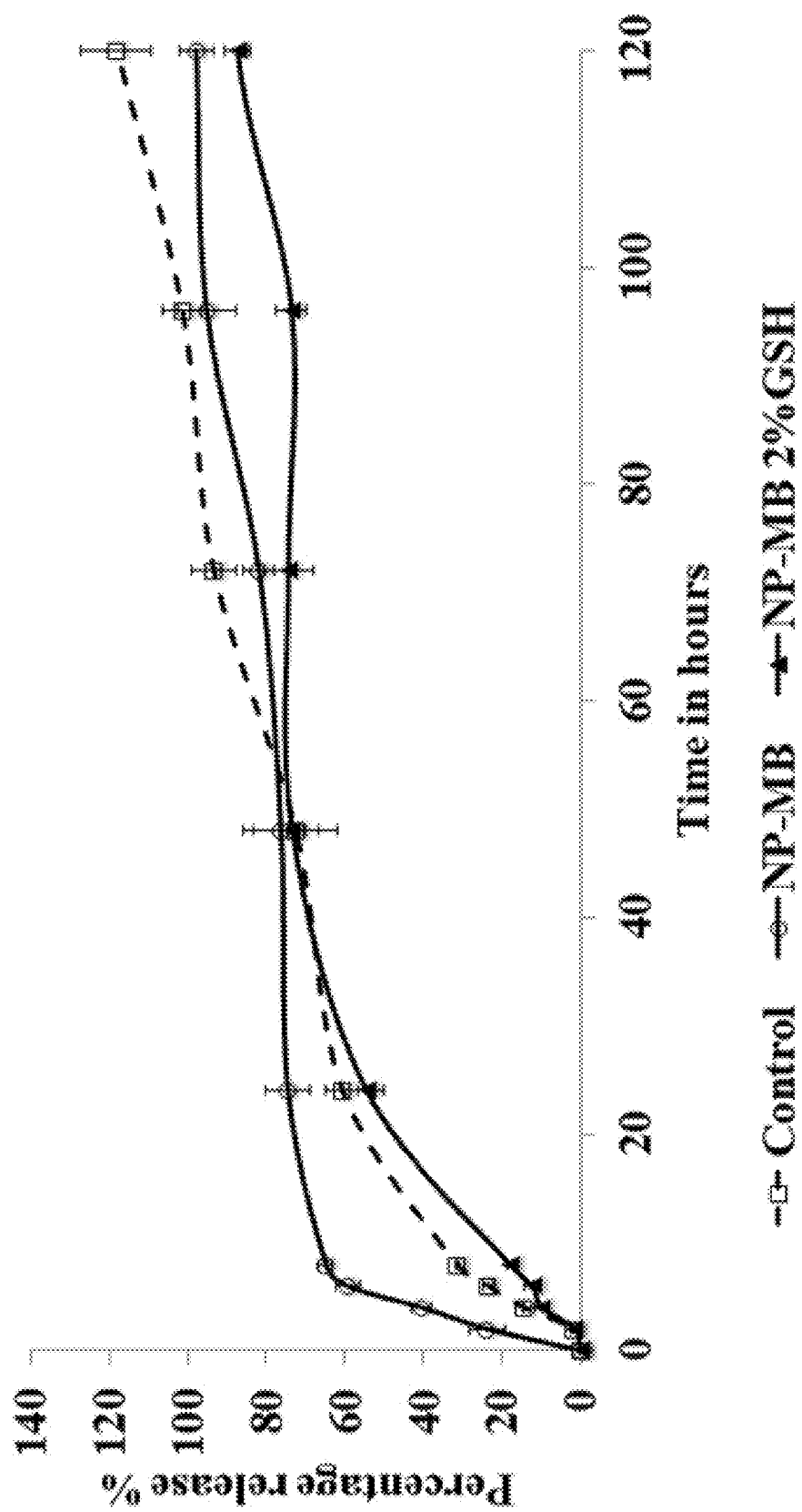
FIG. 3 is a graphical illustration showing in vitro release profile of coated and uncoated MB-NPs (n=6). Cumulative release of the methylene blue from the physical mixture of methylene blue and the polymer, from the nanoparticles, and from the coated nanoparticles is represented. The rate of release from the nanoparticle is faster within first 20 hours and then slower as compared to the mixture. GSH coated nanoparticles demonstrated the slowest sustained release. The release profile confirms the presence of GSH coating. All values shown as a mean n=6 with ±SE. The acronyms can be seen as follows: nanoparticles (NPs), Methylene blue (MB), glutathione reduced (GSH), polydispersity index (PDI).

Both coated and uncoated MB-NPs formulations showed no burst drug release, which may be important for attaining sustained slow release for the optimal therapeutic benefit in treatment (FIG. 3). The initial release phase of up to 6 hours is most likely due to shedding of the MB from the surface of the NPs as the rate of the release is faster than that of the control, where the MB is trapped in the mixture of the polymer. The latter phase (after 8 hours demonstrating slow and sustained release) may be attributed mainly to the diffusion of the MB out of the nanoparticle and partial disintegration of polymer enclosure. The initial higher release for uncoated nanoparticles may be due to the drug present on the surface of the nanoparticles. This was not seen in the physical mixture or in the GSH-coated nanoparticles (as the drug on the surface was coated by the glutathione).

The GSH-coated nanoparticles exhibited a very different release profile characterized both by the absence of the initial rapid release phase seen in uncoated MB-NPs and by the presence of progressive slow release. These findings are consistent with the assumption of formation of the glutathione coating. Specifically, because the MB on the surface of the NPs are displaced by the GSH coating, the initial phase of fast release is not observed. Moreover, the release profile shows that GSH decreases the release rate, perhaps by partially sealing the NPs and slowing down the diffusion of MB out of the NPs, which is evidenced by the slower release rate of MB from GSH-coated NPs than both the control nanoparticles and the uncoated nanoparticles. Overall, GSH-coated nanoparticles demonstrated the necessary controlled and sustained release of MB for the delivery of MB through the BBB, while maintaining tissue saturation levels in the brain.

The effects of NPs on the ability of MB to reduce tau levels were tested in well-characterized cellular models of AD and tauopathies as well [44, 45]. Treatment of GSH-coated MB-NPs showed greater reduction in tau level compared to the MB solution (FIG. 4), demonstrating the capacity of the nanoparticles to effectively allow for delivery of the MB to the cell without compromise in its activity. The more effective reduction in tau levels by GSH-coated NPs may be, perhaps, due to the drastic increase of the reactive surface area as provided by the NPs enclosure, facilitating improved uptake by the cells [30, 40]. Furthermore, a BBB permeation study by using in vitro Transwell system indicated an approximately 8-fold higher permeation of 2% glutathione coated MB-NP compared to the MB solution over 24 hours through the co-culture of RBE4 and C6 cells [46, 47].

Overall, the findings of the study provided a valuable tool and a therapeutic option for the treatment of AD and other related tauopathies. The findings suggest that newly-prepared MB nanoparticles are functionally as effective as MB alone.

Materials and Methods

Materials

PLGA-PEG-COOH (RESOMER RGP d 50105, copolymer ratio 50:50, PEG content 5%) was obtained from BOEHRINGER INGELHEIM CHEMICALS, Inc., Petersburg, Va., USA. Methylene blue was obtained from Sigma. Glutathione (reduced) was obtained from MP BIOMEDICALS, LLC, Solon, Ohio. NaCl, KCl, $Na_2HPO_4$, and $KH_2PO_4$ for phosphate buffered saline (PBS) preparation were obtained from SIGMA-ALDRICH Co., St. Louis, Mo., USA. Acetonitrile, acetone, methanol, trifluoroacetic acid, and triethylamine were HPLC grade purchased from SIGMA-ALDRICH Co., LLC, USA.

All other chemicals used in the study were of analytical grade and were used without any further purification unless specified. Anti-Tau antibody and Anti-GAPDH antibody were purchased from SANTACRUZ BIOTECH and MERIDIAN LIFE SCIENCES, respectively. Cell culture reagents and cell lysis buffer were purchased from INVITROGEN and FISHER SCIENTIFIC, respectively, as described earlier [41].

Preparation of Glutathione Coated PLGA-PEG NPs

NPs made using PLGA-PEG-COOH polymer were synthesized by a nanoprecipitation method described in the art [12, 30]. Briefly, four (4) mg of methylene blue and 100 mg PLGA-PEG-COOH were dissolved in 3 mL of acetone with addition of 100 µL of EtOH to facilitate dissolving of MB. The solution was then added drop-wise into 6 mL of 1% polyvinyl alcohol (PVA) solution, giving a final NPs concentration of 16.67 mg/mL. The optimal ratios of about 0.04 for MB/polymer and about 0.5 for oil/water were maintained for synthesis of the nanoparticles in this experiment. Acetone was then removed from the emulsion by evaporation while stirring at 40° C. To remove unencapsulated drug and emulsifier. NPs were collected by centrifugation at 18,000×g for 35 min. The pellet was suspended in PBS pH 7.4 by sonication and used for further analysis. In order to get 2% glutathione coating, twenty (20) mg glutathione was added per 1 mL of NPs (16.667 mg/mL) and incubated at room temperature for at least 30 minutes before use. The resulting structure can be seen in FIG. 1.

Effects on Particle Size

The particle size and zeta potential of uncoated and glutathione coated PLGA-PEG NPs were measured by the degree of light scattering using MICROTRAC FLEX, MICROTRAC, Inc., PA, USA. The polydispersity index was measured using a DYNAMIPRO plate reader, Wyatt Technology, CA, USA. The NP samples were diluted to fit instrument specifications. In measuring these parameters, the effect of MB loading into the nanoparticle and the effect of presence of reduced glutathione coating on mean particle size and zeta potential of the NPs were studied. Particle size stability was measured by suspending the NPs in PBS and incubating at room temperature (22° C.) for 5 days.

Determination of Entrapment Efficiency (6)

Entrapment efficiency was determined using a method taught in the art [25, 30]. In brief, standard solutions of methylene blue (MB) in methanol were measured by a NANODROP spectrophotometer (NANODROP TECHNOLOGIES Inc., DE USA) at a wavelength of 600 nm to obtain the calibration curve of the drug [42]. The NPs were collected by centrifugation (18,000 rpms for 35 min) and the supernatant removed. The pellet of NPs was solubilized in methanol and allowed to dissolve overnight to extract the drug. The sample was again centrifuged to remove any polymer from the solution, and the amount of solubilized drug was determined by spectroscopy. For the entraption efficiency of glutathione-coated NPs, the pH of the pellet solubilized in methanol was adjusted with access of NaOH to facilitate transformation of clear reduced leuko-MB form to blue MB for quantification by the spectrophotometry. From the standard concentrations in methanol ($r^2$=0.99997), a standard curve was determined and the entrapment efficiency was calculated. All experiments were repeated three times and average values were used. The entrapment efficiency (%) was calculated using the following equation:

$$\text{Entraption efficiency \%} = \frac{MB_{NP}}{MB_{free} - MB_{NP}} \times 100$$

where $MB_{NP}$ represents the amount of methylene blue trapped in the nanoparticle and is quantified from solubilizing the pellet. $MB_{free}$ corresponds to the amount of free methylene blue in the supernatant.

Transmission Electron Microscopy

Examination of nanoparticles morphology, size and shape, was conducted via transmission electron microscopy (TEM) using a JEOL 100S TEM (JEOL Ltd, Tokyo, Japan). Following particle sizing, the sample was diluted 100 times, and ten (10) μL of the NPs solution was carefully placed onto a copper grid coated in a nitrocellulose membrane.

In Vitro Drug Release

The MB release rate from the NPs was measured in PBS (pH 7.4). MB-loaded NPs were placed into a dialysis bag (MWCO 1,000) and suspended in 80 mL of PBS buffer pH 7.4 at 37° C. and stirred at 60 rpms. Samples of 2 mL were collected at predetermined time intervals, and the same volume was replaced with fresh PBS. The volume of each collected fraction was reduced to 250 μL, and the samples were then subjected to analysis by high performance liquid chromatography (HPLC) in duplicate measurements to assess the amount of methylene blue released. Aliquots were analyzed on AGILENT INFINITY 60000 (AGILENT TECHNOLOGIES, CA, USA) using reverse phase Ascentis C-18 100×4.6 mm column with pore size of 2.7 μm.

A modified method was used for the analysis with mobile phase including 80% acetonitrile, 20% water, and 0.1% trifluoroacetic acid, pH 3.0, adjusted with thriethyamine [43]. The flow rate was 0.5 mL/min with injection volume used of 15 μL.

After obtaining a chromatogram, the peak areas were converted to concentrations using a standard curve analyzed simultaneously ($r^2$=0.99673). The percent drug release was then calculated for each sample. Each experiment was repeated three times with technical duplicates, and the average values were used.

Cell Culture, Treatment and Immunoblotting

Endogenous Tau expressing human neuroblastoma SHSY5Y cells and Hela cells stably overexpressing wild-type human tau were maintained in OptiMEM media supplemented with fetal bovine serum and antibiotic solution as described previously [44]. In six-well plates, cells were treated with control or MB-NPs for 24 hours. Cells were harvested and processed for immunoblotting as described previously [45].

Figure 5:
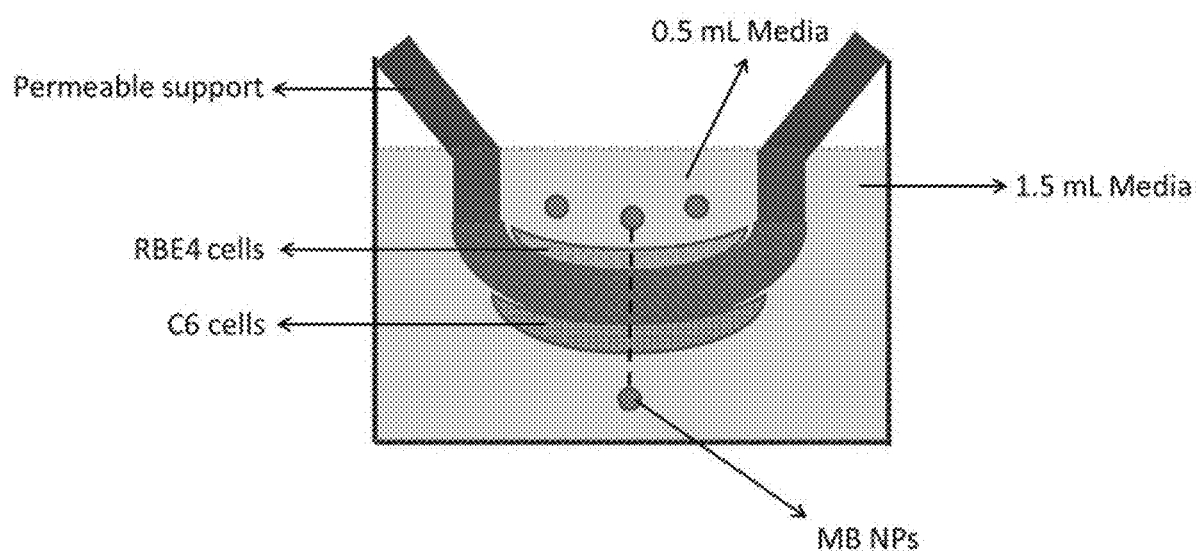
FIG. 5 depicts a setup of Transwell permeable support, suitable for a 12-well plate. Both sides of the insert were coated with rat tail collagen I (BD BIOSCIENCE) before seeding RBE4 and C6 cells to their respective sides in order to establish the co-culture.

In Vitro Blood-Brain Barrier Permeation Assay:

Transwell Permeable Supports (CORNING) with a 0.4 μm pore size were purchased to investigate the permeability of MB nanoparticles across the blood-brain barrier (BBB) [46, 47] (FIG. 5). Each side was coated with 0.1% rat tail collagen I solution diluted from the purchased 100 mg solution (Collagen I, rat tail, 100 mg, BD BIOSCIENCES), left under the hood to adhere to the support for 1 hour, and washed with 200 ML of 1×PBS after aspiration of the remaining collagen solution. The media used was a 1:1 solution of Ham's F10:MEM media (CELLGRO) supplemented with 10% fetal bovine serum (FBS) (INVITROGEN), 1% penicillin and streptomycin (CELLGRO), 0.4 mL of 1 ng/mL human recombinant diluted basic fibroblast growth factor (bFGF) (BD Biosciences), 5 mL of HEPES buffer (FISHER), and 2 mL of a 200 mM stock of L-glutamine (MEDIATECH). 1.5 mL of media was added surrounding the support, and 0.5 mL was added inside the support. This was left to incubate in the incubator (37° C. and 5% $CO_2$) for 24 hours.

After 24 hours, the media was aspirated from the plates. The co-culture was prepared by first seeding $5×10^4$ C6 rat astrocytic cells (ATCC, CCL-107) to the bottom of the support, which remains under the hood for 1 hour, and is subsequently transferred back to the incubator for 2 hours. Next, the remainder media was aspirated, 1.5 mL of media was added to the plate, and the support was reverted back to fit into the well; 0.5 mL of media was added back to the inside of the support. After 48 hours of incubation, the media was aspirated from the inside of the support and $5×10^5$ rat brain endothelial cells (RBE4 cells, gifted by Dr. Aschner of Vanderbilt University Medical Center) were seeded to the inside. 0.5 mL of media was made up after the RBE4 were seeded to the inside of the insert and the plate was placed back in the incubator for 24 hours to allow the cells to adhere (FIG. 5).

Subsequently, the media was aspirated and replaced with equal amounts of 1% FBS experimental media. The co-culture was treated by adding the following to the 0.5 mL of media inside the support: 10 μM of MB drug in solution; uncoated MB-loaded NPs; and 2% glutathione-coated, MB-loaded NPs. Four (4) samples of 100 μL media were taken out from under the support at approximately 0, 3, 6, and 24 hours and fresh experimental media was used to replace the extracted volume. The samples were quantified by UV spectrometry in the SYNERGY H4 plate reader (BIOTEK INSTRUMENTS Inc.) at a wavelength of 600 nm. Data was quantified in triplicates and averaged (n=3).

Statistical Analysis

The data were expressed as the mean of at least three experiments ±standard error.

Statistical comparison between the controls and methylene blue nanoemulsion was performed with paired student t-test to assess the significance of differences. The in vitro release profiles of the NPs and the control were compared by two-way ANOVA analysis using statistical analysis software SAS (SAS INSTITUTE Inc., NC, USA). A five percent (5%) significance level (p-value ≤0.05) was utilized for all statistical analyses.

Results

Physical Parameters of the Nanoparticles

In order to understand the effect of MB loading and GSH coating on the NPs parameters, the physical characteristics of the NPs, such as size, polydispersity index, were evaluated (see Table 1). MB-NPs and coated MB-NPs were compared to the blank NPs containing no drug, which was utilized as a control. Investigation of the sizes of MB-loaded NPs and blank NPs revealed that the average sizes/diameters of each as 150±10 nm and 147.7±4.84 nm, respectively. The average size is the result of quantifying triplicates and obtaining the standard error. The developed NPs demonstrated reduction in size with drug loading, which may be due to more formation of a more compact nanoparticle resulting from the interactions of the polymer with MB. Addition of the GSH coating did not appear to have an effect on the NPs size, where the mean sizes of uncoated NPs (136.5±4.4 nm) and coated NPs (137.8±6.3 nm) were virtually identical. Further, as compared to the control, NPs with 2% glutathione (GSH) coating did not demonstrate a significant change of the mean size (137.8±6.3 nm), perhaps due to more variations in the size attributed to the coating layer [25].

2%. The larger difference in mean size after 5 days in GSH-coated NPs confirms the presence of the GSH coat on the NPs and could be attributed to gradual shedding of GSH.

TABLE 1

Nanoparticle characterization. Nanoparticles loaded with Methylene blue showed significant decrease in the NPs size (p-value = 0.008). Glutathione coating did not significantly alter the nanoparticle size. Zeta potential in MB-NPs did not significantly change as compared to blank NPs. All values shown as a mean of triplicates with ± SE. The acronyms are as follows: nanoparticle (NPs), Methylene blue (MB), glutathione reduced (GSH), polydispersity index (PDI), Entraption efficiency (EE).

| Nanoparticles (NPs) | Size (nm) Mean ± SE | PDI Mean ± SE | Zeta potential mV Mean ± SE | EE % Mean ± SE |
|---|---|---|---|---|
| NPs | 147.7 ± 4.84 | 0.014 ± 0.0003 | −19.21 ± 1.15 | NA |
| MB-NPs | 150 ± 10 | 0.052 ± 0.013 | −7.4 ± 1.39 | 25.07 ± 3.19 |
| 2% GSH-coated MB-NPs | 137.8 ± 6.3 | 0.052 ± 0.013 | −1.84 ± 3.67 | 19.13 ± 0.05 |

Zeta potential describes the surface property of the NPs and is an important factor contributing to the biointeractions of the NPs with its environment [32, 33]. In the current study, NPs, MB-NPs, and coated MB-NPs exhibited negative zeta potential, as follows: −19.21.15 mV, −7.4±11.30 mV, and −1.84±3.67 mV, respectively (Table 1).

In order to ascertain that the batch includes monodisperse NPs of consistent and uniform size, the polydispersity index (PDI) was obtained (Table 1). All NPs formulations followed normal/Gaussian distribution of particle size with PDI value below one (1), confirming narrow distribution of the size of the NPs.

Due to its hydrophilic nature, MB readily dissolves in water phase of the nanoprecipitation approach to synthesis of NPs, thus presenting a challenge to encapsulation by the polymer. However, with the current nanoprecipitation method, a 25.07±3.19% encapsulation of the drug was achieved (see Table 1). The addition of GSH coating may be seen to lower the amount of measured encapsulated drug as the coating replaces the MB inevitably adsorbed at the surface of the NPs.

Effective API delivery requires system stability in physiological solutions. To assess the nanoparticle stability, both coated and uncoated NPs were kept in PBS for at least 5 days, and changes in the mean size and zeta potential were measured (Table 2). No significant changes in the mean particle sizes of MB-NPs and coated MB-NPs were detected. However, GSH-coated NPs decreased in mean size by about 12%, and MB-NPs decreased in mean size by about 2%. The larger difference in mean size after 5 days in GSH-coated NPs confirms the presence of the GSH coat on the NPs and could be attributed to gradual shedding of GSH. Because the changes in mean size were not significant (p-value≤0.05) (i.e., GSH coating is not lost even after 5 days), however, it would be expected that the GSH coating would remain mostly intact in a physiological system.

TABLE 2

Stability of the nanoparticles. Methylene blue nanoparticles exhibited stability over the period of 5 days. The changes in size for all NPs were not significant with p-value ≥ 0.05. Glutathione-coated NPs showed the most of size change due to partial shedding of the GSH coat. All values shown as a mean of triplicates with ± SE. Nanoparticle (NPs), Methylene blue (MB), glutathione reduced (GSH), polydispersity index (PDI).

| | Day 1 | | After 5 days | | |
|---|---|---|---|---|---|
| Nanoparticles | NPs size (nm) | NPs zeta potential (mV) | NPs size (nm) | NPs zeta potential (mV) | Change in mean size, % |
| MB-NPs | 136.5 ± 4.4 | −7.4 ± 11.39 | 135 ± 21.45 | 23.2 ± 12.02 | 2% |
| GSH-coated MB-NPs | 137.8 ± 6.35 | −1.83 ± 3.67 | 121.4 ± 5.24 | 2.07 ± 7.87 | 12% |

NPs Morphology by TEM

Morphology of the MB-NPs was confirmed by transmission electron microscopy (TEM) (FIG. 2). TEM imaging confirmed the nanoparticle size below 200 nm. NPs appeared to have spherical morphology with smooth outer surface and to have consistent size throughout the sample. The TEM allowed for visualization of loading of MB inside of the NPs. Additionally, the GSH coating is visible in causing the nanoparticle to react differently to the beam, resulting in sharper imaging of the nanoparticle edges and of the protrusions on the nanoparticle surface.

In Vitro Release

In this study, the release profile of coated and uncoated MB-NPs was studied in vitro and compared to a control, a physical mixture of the polymer and MB (FIG. 2). Both coated and uncoated NPs demonstrated no burst release. However, the release profile of the uncoated nanoparticles was significantly faster as compared to the control (p-value<0.001) with approximately 60% of MB released within 10 hours; after approximately 10 hours, the release of MB appears to proceed at a slower rate. Through the duration of the study, the control released MB at approximately constant rate by diffusion of MB out of the mixture. GSH-coated NPs exhibited a slower release as compared to the control and uncoated nanoparticles. For about 8 hours of release, the coated NPs demonstrated significantly slower release rate as compared to the uncoated NPs (p-value<0.001). After 24 hours, the release of MB from coated NPs appeared to be comparable to that of the uncoated nanoparticles. Thus, the release of the drug from the GSH-coated NPs can be characterized as a slow and sustained release for up to 120 hours.

Effect of Nanoparticles on Tau Levels in Cultured Cells

To test the functionality of newly generated NPs, two different cell culture-based AD models were utilized. Endogenously tau expressing SHSHY neuronal cells and stably tau overexpressing HeLa cells were treated with 5 µM and 10 µM of MB-NPs, coated MB-NPs, control NPs, vehicle, and/or drug MB-solution for 24 hours. Cells were harvested, and samples were analyzed for tau levels by immunoblotting (FIG. 4). The GSH-coated MB-NPs formulation showed greater reduction in tau level compared to MB solution (FIG. 4) at 5 µm and 10 µm concentrations in both endogenous tau and over-expressing tau cell lines. The tau reduction level was almost similar for coated and uncoated NPs in both cell lines.

In Vitro Blood-Brain Barrier Permeation Assay

Figure 6:
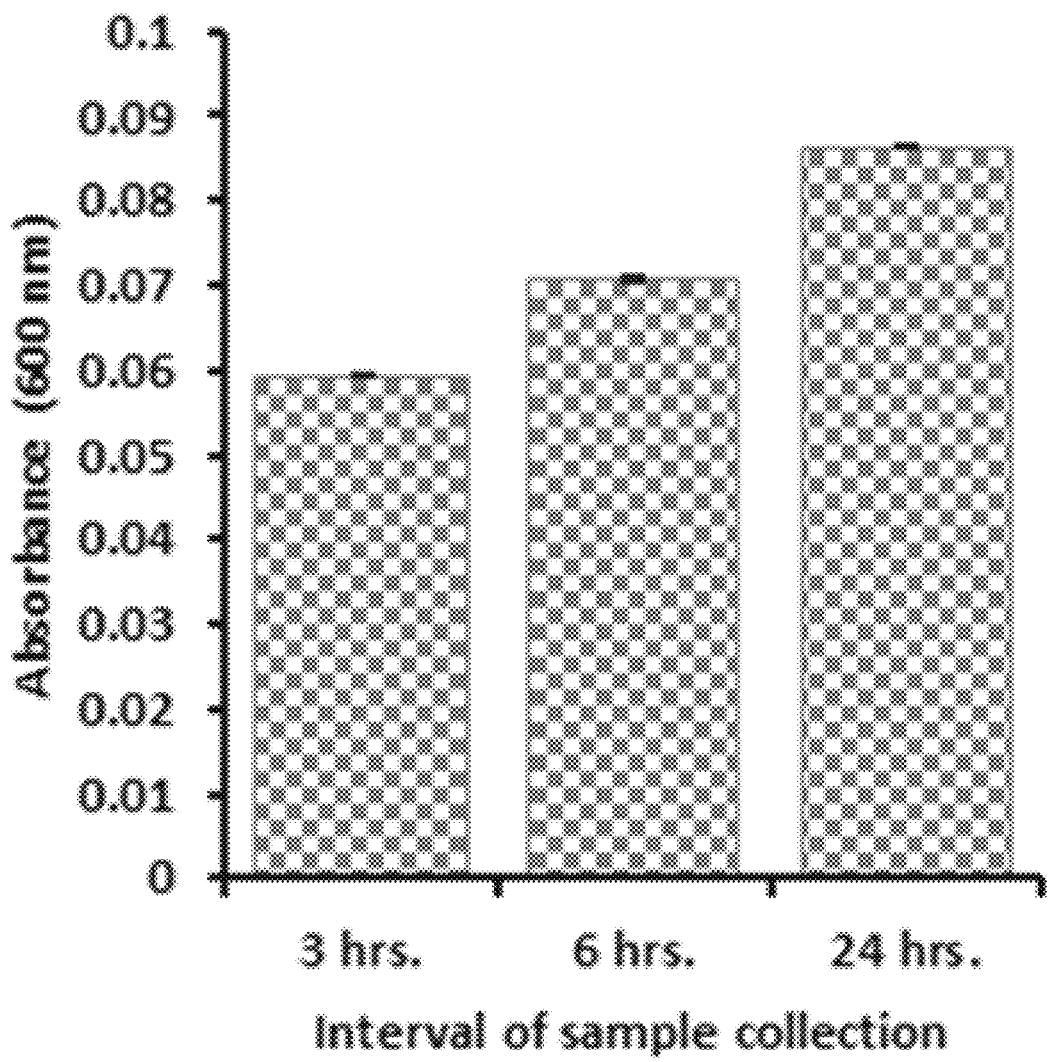
FIG. 6 is a graphical illustration showing permeation of 10 µM of 2% glutathione-coated nanoparticles. 100 µL of the media was extracted from below the permeable support at approximately 0, 3, 6, and 24 hours; setup was replenished with fresh media. The results were quantified by UV spectroscopy at a wavelength of 600 nm. Quantification of the results and standard deviation represents an average of quantified triplicates (n=3).
Figure 7:
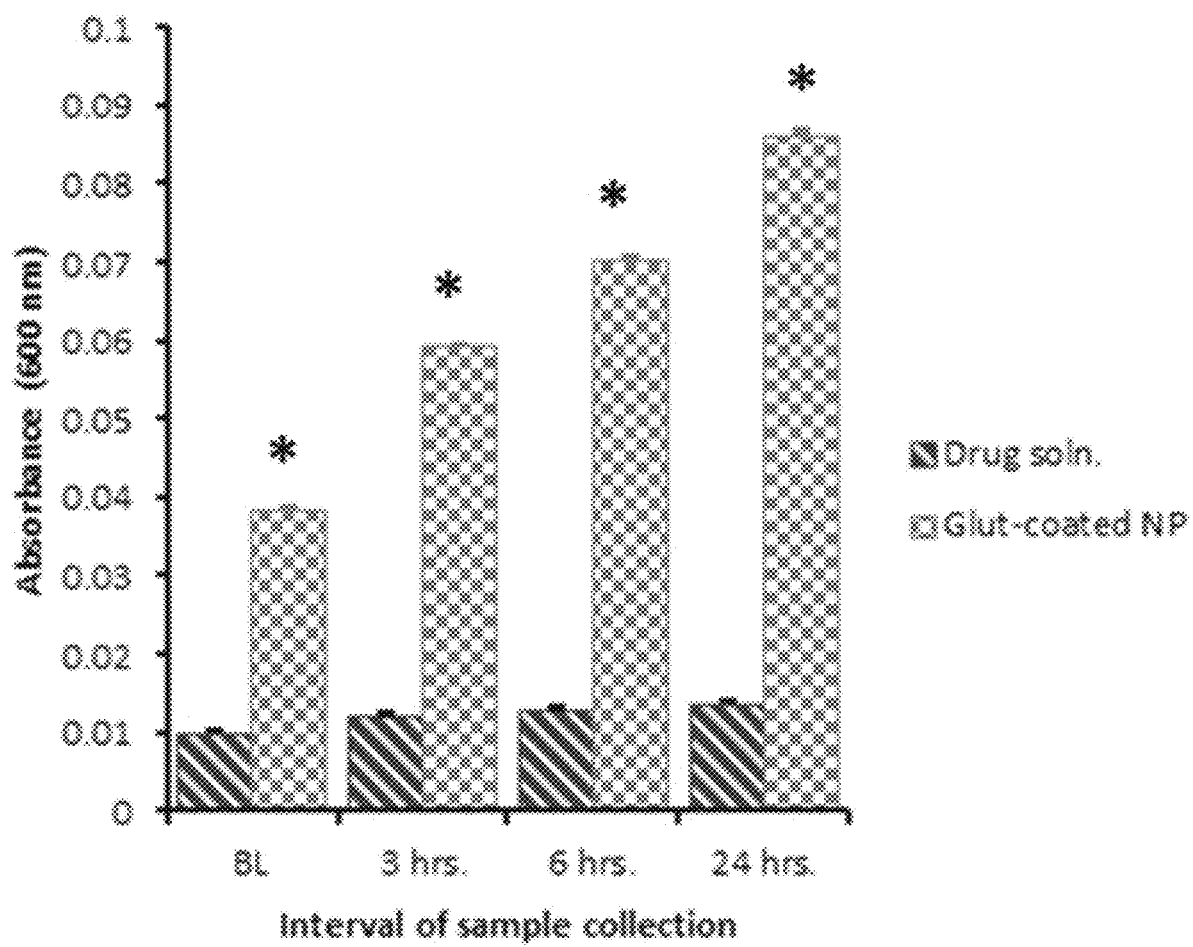
FIG. 7 is a graphical illustration comparing permeation of 10 µM of free MB drug solution versus 2% glutathione-coated NP. 100 µL of the media was extracted from below the permeable support at approximately 0, 3, 6, and 24 hours; setup was replenished with fresh media. The results were quantified by UV spectroscopy at a wavelength of 600 nm. Quantification of the results and standard deviation represents average of quantified triplicates (n=3). Fluorescence data regarding free drug solution yielded by spectroscopy was reduced by 75% to mimic approximately 25% entrapment efficiency of the MB drug by NPs as indicated herein. Data for the 2% glutathione-coated nanoparticles was statistically significantly higher than data for the free MB drug solution (p<0.05).

FIGS. 6 and 7 illustrate the data from the in vitro BBB permeation of the MB drug solution and the glutathione-coated nanoparticles. Ten (10) µM of the 2% glutathione-coated nanoparticles showed the highest level of permeation across the simulated BBB. There was a linear increase in the permeation of glutathione-coated nanoparticles permeating the BBB over 24 hours (FIG. 6). The glutathione-coated nanoparticles were seen to be more effective at permeating the BBB model than the free MB drug solution (FIG. 7); data has statistical significance with p<0.05. The data of the permeation of the free MB drug solution was decreased by 75% to mimic the approximately 25% entrapment efficiency exhibited by the MB-loaded nanoparticles, as described previously. While the permeation of glutathione-coated MB nanoparticles increased linearly over the 24-hour period, the permeation of the free MB drug solution remained relatively constant over the same period.

LIST OF REFERENCES

[1] Gura, T. Hope in Alzheimer's Fight Emerges from Unexpected Places, Nature medicine, 2008, 14(9), 894.

[2] Barten, D. M., and Albright, C. F. Therapeutic Strategies for Alzheimer's Disease. Molecular neurobiology, 2008, 37(2-3), 171-186.

[3] Friedhoff, P., Von Bergen, M., Mandelkow, E. M., and Mandelkow, E. Structure of Tau Protein and Assembly into Paired Helical Filaments, Biochimica et biophysica acta, 2000, 1502(1), 122-132.

[4] Chu, L. W. Alzheimer's Disease: Early Diagnosis and Treatment, Hong Kong medical journal=Xianggang yi xue za zhi/Hong Kong Academy of Medicine, 2012, 18(3), 228-237.

[5] Ward, S. M., Himmelstein, D. S., Lancia, J. K., and Binder, L. I. Tau Oligomers and Tau Toxicity in Neurodegenerative Disease, Biochemical Society transactions, 2012, 40(4), 667-671.

[6] Taniguchi, S., Suzuki, N., Masuda, M., Hisanaga, S., Iwatsubo, T., Goedert, M., and Hasegawa, M. Inhibition of Heparin-Induced Tau Filament Formation by Phenothiazines, Polyphenols, and Porphyrins, The Journal of biological chemistry, 2005, 280(9), 7614-7623.

[7] Congdon, E. E., Wu, J. W., Myeku, N., Figueroa, Y. H., Herman, M., Marinec, P. S., Gestwicki, J. E., Dickey, C. A., Yu, W. H., and Duff, K. E. Methylthioninium Chloride (Methylene Blue) Induces Autophagy and Attenuates Tauopathy in vitro and in vivo, Autophagy, 2012, 8(4), 609-622.

[8] Pritchard, S. M., Dolan, P. J., Vitkus, A., and Johnson, G. V. The Toxicity of Tau in Alzheimer Disease: Turnover, Targets and Potential Therapeutics, Journal of cellular and molecular medicine, 2011, 15(8), 1621-1635.

[9] Schirmer, R. H., Adler, H., Pickhardt, M., and Mandelkow, E. "Lest We Forget You—Methylene Blue . . . ", Neurobiology of aging, 2011, 32(12), 2325 e2327-2316.

[10] Duan, Y., Haugabook, S. J., Sahlcy, C. L., and Muller, K. J. Methylene Blue Blocks Cgmp Production and Disrupts Directed Migration of Microglia to Nerve Lesions in the Leech Cns, Journal of neurobiology, 2003, 57(2), 183-192.

[11] Riha, P. D., Bruchey, A. K., Echevarria, D. J., and Gonzalez-Lima, F. Memory Facilitation by Methylene Blue: Dose-Dependent Effect on Behavior and Brain Oxygen Consumption, European journal of pharmacology, 2005, 511(2-3), 151-158.

[12] Atamna, H., Nguyen, A., Schultz, C., Boyle, K., Newberry, J., Kato, H., and Ames, B. N. Methylene Blue Delays Cellular Senescence and Enhances Key Mitochondrial Biochemical Pathways, FASEB journal: official publication of the Federation of American Societies for Experimental Biology, 2008, 22(3). 703-712.

[13] Deiana, S., Harrington, C. R., Wischik, C. M., and Riedel, G. Methylthioninium Chloride Reverses Cognitive Deficits Induced by Scopolamine: Comparison with Rivastigmine, Psychopharmacology, 2009, 202(1-3), 53-65.

[14] Harvey, B. H., Duvenhage, I., Viljoen, F., Scheepers, N., Malan, S. F., Wegener, G., Brink, C. B., and Petzer, J. P. Role of Monoamine Oxidase, Nitric Oxide Synthase and Regional Brain Monoamines in the Antidepressant-Like Effects of Methylene Blue and Selected Structural Analogues, Biochemical pharmacology, 2010, 80(10), 1580-1591.

[15] Oz, M., Lorke, D. E., and Petroianu, G. A. Methylene Blue and Alzheimer's Disease, Biochemical pharmacology, 2009, 78(8), 927-932.

[16] Khakpay, R., Polster, D., Koles, L., Skorinkin, A., Szabo, B., Wirkner, K., and Illes, P. Potentiation of the Glutamatergic Synaptic Input to Rat Locus Coeruleus Neurons by P2x7 Receptors, Purinergic signalling, 2010, 6(3), 349-359.

[17] Hosokawa, M., Arai, T., Masuda-Suzukake, M., Nonaka, T., Yamashita, M., Akiyama, H., and Hasegawa, M. Methylene Blue Reduced Abnormal Tau Accumulation in P3011 Tau Transgenic Mice, PloS one, 2012, 7(12), e52389.

[18] O'leary, J. C., 3rd, Li, Q., Marinec, P., Blair, L. J., Congdon, E. E., Johnson, A. G., Jinwal, U. K., Koren, J., 3rd, Jones, J. R., Kraft, C., Peters. M., Abisambra, J. F., Duff, K. E., Weeber, E. J., Gestwicki, J. E., and Dickey, C. A. Phenothiazine-Mediated Rescue of Cognition in Tau Transgenic Mice Requires Neuroprotection and Reduced Soluble Tau Burden, Molecular neurodegeneration, 2010, 5(45.

[19] Albanese, A., Tang, P. S., and Chan, W. C. The Effect of Nanoparticle Size, Shape, and Surface Chemistry on Biological Systems, Annu Rev Biomed Eng, 2012, 14(1-16.

[20] Chaisri, W., Hennink, W. E., and Okonogi, S. Preparation and Characterization of Cephalexin Loaded Plga Microspheres, Curr Drug Deliv, 2009, 6(1), 69-75.

[21] Yadav, K. S., and Sawant, K. K. Formulation Optimization of Etoposide Loaded Plga Nanoparticles by Double Factorial Design and Their Evaluation, Curr Drug Deliv, 2010, 7(1), 51-64.

[22] Muthu, M. S., and Singh, S. Poly (D, L-Lactide) Nanosuspensions of Risperidone for Parenteral Delivery: Formulation and in-Vitro Evaluation, Curr Drug Deliv, 2009, 6(1), 62-68.

[23] Kumar, P. V., Agashe, H., Dutta, T., and Jain, N. K. Pegylated Dendritic Architecture for Development of a Prolonged Drug Delivery System for an Antitubercular Drug, Curr Drug Deliv, 2007, 4(1), 11-19.

[24] Lockman, P. R., Oyewumi, M. O., Koziara, J. M., Roder, K. E., Mumper, R. J., and Allen, D. D. Brain Uptake of Thiamine-Coated Nanoparticles, J Control Release, 2003, 93(3), 271-282.

[25] Geldenhuys, W., Mbimba, T., Bui, T., Harrison, K., and Sutariya, V. Brain-Targeted Delivery of Paclitaxel Using Glutathione-Coated Nanoparticles for Brain Cancers, J Drug Target, 2011, 19(9), 837-845.

[26] Kreuter, J. Nanoparticulate Systems for Brain Delivery of Drugs, Adv Drug Deliv Rev, 2001, 47(1), 65-81.

[27] Xie, J., Lei, C., Hu, Y., Gay, G. K., Bin Jamali, N. H., and Wang, C. H. Nanoparticulate Formulations for Paclitaxel Delivery across Mdck Cell Monolayer, Current pharmaceutical design, 2010, 16(21), 2331-2340.

[28] Olivier, J. C., Huertas, R., Lee, H. J., Calon, F., and Pardridge, W. M. Synthesis of Pegylated Immunonanoparticles, Pharmaceutical research, 2002, 19(8), 1137-1143.

[29] Olivier, J. C., Fenart, L., Chauvet, R., Pariat, C., Cecchelli, R., and Couet, W. Indirect Evidence That Drug Brain Targeting Using Polysorbate 80-Coated Polybutylcyanoacrylate Nanoparticles Is Related to Toxicity, Pharmaceutical research, 1999, 16(12), 1836-1842.

[30] Carroll, R. T., Bhatia, D., Geldenhuys, W., Bhatia, R., Miladore, N., Bishayee, A., and Sutariya, V. Brain-Targeted Delivery of Tempol-Loaded Nanoparticles for Neurological Disorders, J Drug Target, 2010, 18(9), 665-674.

[31] Gratton, S. E., Ropp, P. A., Pohlhaus, P. D., Luft, J. C., Madden, V. J., Napier, M. E., and Desimone, J. M. The Effect of Particle Design on Cellular Internalization Pathways, Proc Natl Acad Sci USA, 2008, 105(33). 11613-11618.

[32] Lynch, I., Salvati, A., and Dawson, K. A. Protein-Nanoparticle Interactions: What Does the Cell See?, Nat Nanotechnol, 2009, 4(9), 546-547.

[33] Elsaesser, A., and Howard, C. V. Toxicology of Nanoparticles, Adv Drug Deliv Rev, 2012, 64(2), 129-137.

[34] Wang, A.-J., Jian, C.-H., Li, S.-D., Lin, Y.-F., and Liu, S.-J. Glutathione Based Delivery System; Editor, Ed.; Google Patents: City, 2008; Vol.,

[35] Liu, R. M. Down-Regulation of Gamma-Glutamylcysteine Synthetase Regulatory Subunit Gene Expression in Rat Brain Tissue During Aging, Journal of neuroscience research, 2002, 68(3), 344-351.

[36] Parihar, M. S., Kunz, E. A., and Brewer, G. J. Age-Related Decreases in Nad(P)H and Glutathione Cause Redox Declines before Atp Loss During Glutamate Treatment of Hippocampal Neurons, Journal of neuroscience research, 2008, 86(10), 2339-2352.

[37] Rebrin, I., Forster, M. J., and Sohal, R. S. Effects of Age and Caloric Intake on Glutathione Redox State in Different Brain Regions of C57bl/6 and Dba/2 Mice, Brain research, 2007, 1127(1). 10-18.

[38] Robillard, J. M., Gordon. G. R., Choi, H. B., Christie, B. R., and Macvicar. B. A. Glutathione Restores the Mechanism of Synaptic Plasticity in Aged Mice to That of the Adult, PloS one, 2011, 6(5), e20676.

[39] Sasaki, T., Senda, M., Kim, S., Kojima, S., and Kubodera, A. Age-Related Changes of Glutathione Content, Glucose Transport and Metabolism, and Mitochondrial Electron Transfer Function in Mouse Brain. Nuclear medicine and biology, 2001, 28(1), 25-31.

[40] Geldenhuys, W., Mbimba, T., Bui, T., Harrison, K., and Sutariya, V. Brain-Targeted Delivery of Paclitaxel Using Glutathione-Coated Nanoparticles for Brain Cancers, Journal of drug targeting, 2011, 19(9), 837-845.

[41] Jinwal, U. K., Akoury, E., Abisambra, J. F., O'leary, J. C., 3rd, Thompson, A. D., Blair, L. J., Jin, Y., Bacon, J., Nordhues, B. A., Cockman, M., Zhang, J., Li, P., Zhang, B., Borysov, S., Uversky, V. N., Biernat, J., Mandelkow, E., Gestwicki, J. E., Zweckstetter, M., and Dickey, C. A. Imbalance of Hsp70 Family Variants Fosters Tau Accumulation, FASEB journal: official publication of the Federation of American Societies for Experimental Biology, 2013, 27(4), 1450-1459.

[42] Park, J., Fong, P. M., Lu, J., Russell, K. S., Booth, C. J., Saltzman, W. M., and Fahmy, T. M. Pegylated Plga Nanoparticles for the Improved Delivery of Doxorubicin, Nanomedicine: nanotechnology, biology, and medicine, 2009, 5(4), 410-418.

[43] Sobal, G., Rodrigues, M., and Sinzinger, H. Radioiodinated Methylene Blue—a Promising Agent for Melanoma Scintigraphy: Labelling, Stability and in vitro Uptake by Melanoma Cells, Anticancer Res, 2008, 28(6A), 3691-3696.

[44] Jinwal, U. K., Miyata, Y., Koren, J., 3rd, Jones, J. R., Trotter, J. H., Chang, L., O'leary, J., Morgan, D., Lee, D. C., Shults, C. L., Rousaki, A., Weeber, E. J., Zuiderweg, E. R., Gestwicki, J. E., and Dickey, C. A. Chemical Manipulation of Hsp70 Atpase Activity Regulates Tau Stability. The Journal of neuroscience: the official journal of the Society for Neuroscience, 2009, 29(39), 12079-12088.

[45] Abisambra, J., Jinwal, U. K., Miyata, Y., Rogers, J., Blair, L., Li, X., Seguin, S. P., Wang, L., Jin, Y., Bacon, J., Brady, S., Cockman, M., Guidi, C., Zhang, J., Koren, J., Young, Z. T., Atkins, C. A., Zhang, B., Lawson, L. Y., Weeber, E. J., Brodsky, J. L., Gestwicki, J. E., and Dickey, C. A. Allosteric Heat Shock Protein 70 Inhibitors Rapidly Rescue Synaptic Plasticity Deficits by Reducing Aberrant Tau, Biological psychiatry, 2013.

[46] Etame, A. B., Smith, C. A., Chan, W. C. W., Rutka, J. T. Design and Potential Application of PEGylated Gold Nanoparticles with Size-Dependent Permeation Through Brain Microvasculature, Nanomedicine: Nanotechnology, Biology, and Medicine, 2011, 7, 992-1000.

[47] Garberg, P., Ball, M., Borg, N., Cecchelli, R., Fenart, L., Hurst R. D., Lindmark, T., Mabondzo, A., Nilsson, J. E., Raub, T. J., Stanimirovic, D., Terasaki, T., Oberg, J. O., Osterberg, T. In vitro Models for the Blood-Brain Barrier. Toxicol in vitro, 2005, 19, 299-334.

[48] Rempe, R., Cramer. S., Huwel. S., and Galla, H. J. Transport of Poly(N-Butylcyano-Acrylate) Nanoparticles across the Blood-Brain Barrier in vitro and Their Influence on Barrier Integrity, Biochemical and biophysical research communications, 2011, 406(1), 64-69.

[49] Pardridge, W. M. Blood-Brain Barrier Delivery, Drug discovery today, 2007, 12(1-2), 54-61.

[50] Pardridge, W. M. Blood-Brain Barrier Drug Targeting: The Future of Brain Drug Development, Molecular interventions, 2003, 3(2), 90-105, 151.

[51] Saija, A., Princi, P., Trombetta, D., Lanza, M., and De Pasquale, A. Changes in the Permeability of the Blood-Brain Barrier Following Sodium Dodecyl Sulphate Administration in the Rat, Experimental brain research. Experimentelle Himforschung. Experimentation cerebrale, 1997, 115(3), 546-551.

[52] Koziara, J. M., Lockman, P. R., Allen, D. D., and Mumper, R. J. In Situ Blood-Brain Barrier Transport of Nanoparticles, Pharmaceutical research, 2003, 20(11), 1772-1778.

[53] Costantino, L., and Boraschi, D. Is There a Clinical Future for Polymeric Nanoparticles as Brain-Targeting Drug Delivery Agents?, Drug discovery today, 2012, 17(7-8), 367-378.

[54] Mu, L., and Feng, S. S. A Novel Controlled Release Formulation for the Anticancer Drug Paclitaxel (Taxol): Plga Nanoparticles Containing Vitamin E Tpgs, J Control Release, 2003, 86(1), 33-48.

[55] Wischke, C., and Schwendeman, S. P. Principles of Encapsulating Hydrophobic Drugs in Pla/Plga Microparticles, Int J Pharm, 2008, 364(2), 298-327.

Jinwal K. Umesh, et al., Methylene blue loaded nanoparticles for treatment of Alzheimer's disease and other tauopathies, Nanoflorida 2012, 29 Sep. 2012, USF, Tampa, Fla.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

GLOSSARY OF CLAIM TERMS

Controlled and sustained release: This term is used herein to refer to release or delivery of pharmaceutical agent in response to a stimulus or time. As seen herein, a controlled and sustained release of pharmaceutical agent (e.g., methylene blue) was achieved through the glutathione coating that breaks down over time to release the pharmaceutical agent contained within the layer of nanoparticles.

Extends outwardly: This term is used herein to refer to projecting externally from the surface of an object. Thus, a spacer and connected hydrophilic group—that extends outwardly from a layer of nanoparticles that substantially encloses a pharmaceutical agent-projects externally away from the interior of that enclosure, such that the hydrophilic group can interact with the external environment prior to the nanoparticles.

Hydrophobic, protective coating: This term is used herein to refer to a covering around the outer surface of a layer of nanoparticles, where the covering is capable of traversing a hydrophobic environment, such as the BBB.

Substantially encloses: This term is used herein to refer to surrounding a majority, or nearly all, of something. For example, a layer of nanoparticles can substantially enclose a pharmaceutical agent, such as methylene blue, by surrounding a majority of the pharmaceutical agent. In some situations, as discussed previously, methylene blue has been seen to diffuse through the BBB prior to breakdown of the polymer-based layer of nanoparticles.

Targeted region: This term is used herein to refer to an area within a subject's body in need of delivery of a pharmaceutical agent (e.g., methylene blue). An example of a targeted region is the brain of a subject.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A nanoparticle drug composition comprising:
    at least one nanoparticle comprising a poly(lactic-co-glycolic acid) polymer conjugated to polyethylene glycol (PEG) linked to a hydrophilic group wherein the nanoparticle is coated with glutathione; and
    a hydrophilic pharmaceutically active agent encapsulated within the at least one nanoparticle at an entrapment efficiency of about 19% wherein the hydrophilic pharmaceutically active agent is methylene blue;
    wherein the nanoparticle drug composition is generated by a process consisting essentially of:
        dissolving or diluting the poly(lactic-co-glycolic acid) polymer conjugated to the polyethylene glycol (PEG) linked to the hydrophilic group and a predetermined quantity of the hydrophilic pharmaceutically active agent in an amount of acetone and an amount of ethanol to form a solution;
        adding the solution to a polyvinyl alcohol (PVA) solution to form an emulsion;
        evaporating the acetone from the emulsion wherein upon evaporation of the acetone, at least one nanoparticle is generated;
        centrifuging the emulsion to remove unencapsulated hydrophilic pharmaceutically active agent and the PVA; and
        coating the at least one nanoparticle with the glutathione.

2. The nanoparticle drug composition of claim 1, wherein the hydrophilic group is a carboxyl group.

3. The nanoparticle drug composition of claim 1, wherein the at least one glutathione-coated nanoparticle has a diameter of between about 100 nm to about 150 nm.

4. The nanoparticle drug composition of claim 1, wherein the ratio of the hydrophilic pharmaceutically active agent to the poly(lactic-co-glycolic acid) polymer is about 0.04.

5. A method of reducing tau levels in a brain of a patient suffering from Alzheimer's disease or other related taupathies characterized by increased tau levels comprising:
    administering a therapeutically effective amount of a nanoparticle drug composition according to claim 1 wherein the hydrophilic pharmaceutical agent is methylene blue.

6. The method of claim 5, wherein the hydrophilic group is a carboxyl group.

7. The method of claim 5, wherein the disease is Alzheimer's disease.

8. The method of claim 5, wherein the nanoparticles have a diameter of between about 100 nm to about 150 nm.

* * * * *